United States Patent
Shah et al.

(10) Patent No.: US 11,285,163 B2
(45) Date of Patent: Mar. 29, 2022

(54) OPHTHALMIC SOLUTION

(71) Applicant: SENTISS PHARMA PRIVATE LIMITED, New Delhi (IN)

(72) Inventors: Mandar V. Shah, New Delhi (IN); Deepak Bahri, New Delhi (IN)

(73) Assignee: Sentiss Pharma Private Limited, New Delhi (IN)

( * ) Notice: Subject to any disclaimer, the term of this patent is extended or adjusted under 35 U.S.C. 154(b) by 0 days.

(21) Appl. No.: 15/520,217

(22) PCT Filed: Oct. 16, 2015

(86) PCT No.: PCT/IB2015/057963
§ 371 (c)(1),
(2) Date: Apr. 19, 2017

(87) PCT Pub. No.: WO2016/063184
PCT Pub. Date: Apr. 28, 2016

(65) Prior Publication Data
US 2017/0304316 A1    Oct. 26, 2017

(30) Foreign Application Priority Data

Oct. 20, 2014  (IN) .............................. 2985DEL2014

(51) Int. Cl.
| A61K 31/5575 | (2006.01) |
| A61K 47/26 | (2006.01) |
| A61K 45/06 | (2006.01) |
| A61K 9/00 | (2006.01) |
| A61K 47/34 | (2017.01) |
| A61K 31/5377 | (2006.01) |
| A61K 31/542 | (2006.01) |

(52) U.S. Cl.
CPC ........ A61K 31/5575 (2013.01); A61K 9/0048 (2013.01); A61K 31/5377 (2013.01); A61K 31/542 (2013.01); A61K 45/06 (2013.01); A61K 47/26 (2013.01); A61K 47/34 (2013.01); A61K 2300/00 (2013.01)

(58) Field of Classification Search
CPC .............. A61K 2300/00; A61K 31/542; A61K 31/5575; A61K 31/5377; A61K 45/06; A61K 47/26; A61K 47/34; A61K 9/0048; A61P 27/02; A61P 27/06; A61P 43/00
See application file for complete search history.

(56) References Cited

U.S. PATENT DOCUMENTS

| 5,378,703 A * | 1/1995 | Dean .................... C07D 333/34 514/222.8 |
| 6,264,935 B1 * | 7/2001 | Chastaing ............ A61K 9/0048 424/427 |
| 2009/0234004 A1 | 9/2009 | Kabra et al. |
| 2013/0035338 A1 * | 2/2013 | Tang .................... A61K 31/382 514/236.2 |
| 2013/0157963 A1 | 6/2013 | Gore et al. |

FOREIGN PATENT DOCUMENTS

| EP | 2070518 | 6/2009 |
| JP | 2010037327 | 2/2010 |
| WO | WO9115486 | 10/1991 |
| WO | WO9825620 | 6/1998 |
| WO | WO08027340 | 3/2008 |
| WO | WO11067791 | 6/2010 |
| WO | WO12009696 | 1/2012 |
| WO | WO-2013090842 A2 * | 6/2013 ............. A61K 47/32 |
| WO | WO13139444 | 9/2013 |
| WO | WO15110993 | 7/2015 |
| WO | WO16063184 | 4/2016 |

OTHER PUBLICATIONS

Sandoz, Package Leaflet, Information for the User, Sep. 2014. (Year: 2014).*
International Search Report for International Appln. No. PCT/IB2015/057963 dated Oct. 16, 2015 (8 pgs.).
Written Opinion of the International Searching Authority for International Appl. No. PCT/IB2015/057963 dated Oct. 16, 2015 (10 pgs.).
"COSOPT", Nov. 1, 2012 (Nov. 1, 2012), XP055236426, Retrieved from the Internet: URL:https://www.merck.com/product/usa/pi_circulars/c/cosopt/cosopt_pi.pdf [retrieved on Dec. 15, 2015] p. 1.

* cited by examiner

*Primary Examiner* — Jean P Cornet
(74) *Attorney, Agent, or Firm* — Fish & Richardson P.C.

(57) ABSTRACT

Disclosed herein an ophthalmic formulation comprises carbonic anhydrase inhibitor(s) alone, in an aqueous solution or a combination of two intraocular pressure (IOP) reducing and/or glaucoma treatment agents or a combination of three intraocular pressure (IOP) reducing and/or glaucoma treatment agents and a manufacturing process thereof.

The present invention further relates to the composition(s) manufactured by the process described herein and methods for treating persons suffering from glaucoma or ocular hypertension.

In particular, the persons are treated with carbonic anhydrase inhibitor(s) alone or a combination of two intraocular pressure (IOP) reducing and/or glaucoma treatment agents or a combination of three intraocular pressure (IOP) reducing and/or glaucoma treatment agents to control their intraocular pressure (IOP).

Further disclosed herein the formulations as manufactured relate to a highly solubilized form of poorly insoluble drugs/active ingredient(s) to improve its bio-availability and manufacturability.

12 Claims, No Drawings

OPHTHALMIC SOLUTION

CROSS-REFERENCE TO RELATED APPLICATIONS

This application is a 35 U.S.C. § 371 National Stage Application of International Application No. PCT/IB2015/057963, filed Oct. 16, 2015, which claims priority to Provisional Indian Patent Application No. 2985/DEL/2014, filed on 20 Oct. 2014, the contents of each of which are incorporated by reference herein in their entirety.

FIELD OF THE INVENTION

The present invention relates to an ophthalmic formulation which comprises carbonic anhydrase inhibitor(s) (CAIs) alone, in an aqueous solution and a manufacturing process thereof.

The ophthalmic formulation(s) of the present invention can also be used in combination with a second therapeutically active agent(s) to a mammal in need thereof, wherein said second therapeutically active agent is selected from, but not limited to, beta-blockers, prostaglandin analogs, prostamides, alpha 2-adrenergic agonists, miotics, neuroprotectants and combinations thereof.

The ophthalmic formulation(s) of the present invention can also be used in combination with a third therapeutically active agent(s) to a mammal in need thereof, wherein said third therapeutically active agent is selected from, but not limited to, beta-blockers, prostaglandin analogs, prostamides, alpha 2-adrenergic agonists, miotics, neuroprotectants and combinations thereof.

The present invention relates to an ophthalmic formulation comprises carbonic anhydrase inhibitor(s) alone, in an aqueous solution and/or in combination with second intraocular pressure (IOP) reducing and/or glaucoma treatment agents or further in combination of third intraocular pressure (IOP) reducing and/or glaucoma treatment agents and methods(s) of manufacturing process thereof.

The present invention further relates to the composition(s) manufactured by the process described herein and methods for treating persons suffering from glaucoma or ocular hypertension.

BACKGROUND OF THE INVENTION

Brinzolamide is a carbonic anhydrase inhibitor used to lower intraocular pressure in patients with ocular hypertension or open-angle glaucoma. Brinzolamide is chemically (R)-(+)-4-ethylamino-2-(3-methoxypropyl)-3,4-dihydro-2H-thieno[3,2-e]-1,2-thiazine-6-sulfonamide-1,1-dioxide and has the empirical formula $C_{12}H_{21}N_3O_5S_3$. Brinzolamide has a molecular weight of 383.5 and a melting point of about 131° C.

This compound is disclosed in U.S. Pat. No. 5,378,703 (Dean, et al.). The compound is also disclosed in European patent EP 527801. U.S. Pat. No. 6,071,904 discloses processes for preparation of brinzolamide ophthalmic composition.

Brinzolamide in the form of ophthalmic suspension is developed and marketed by Alcon Laboratories Inc. in United States under the brand name Azopt® (brinzolamide ophthalmic suspension 1%). Brinzolamide suspension is indicated for lowering elevated intra-ocular pressure (IOP) in patients with open-angle glaucoma or ocular hypertension (OHT).

Various methods or techniques have been disclosed in the prior for the preparation of brinzolamide ophthalmic suspension.

International patent application WO 98/25620 teaches that conventional sterilization methods cannot be employed in the manufacture of suspensions comprising brinzolamide since the compound recrystallizes as large needle-shaped crystals, upon cooling, after autoclaving. According to WO 98/25620, dry heat sterilization is also not suitable, since it causes melting of the material, whereas sterilization by ethylene oxide and gamma irradiation introduces unacceptable degradation products.

EP0941094 discloses a process for making brinzolamide suspension by autoclaving of concentrated slurry of brinzolamide and tyloxapol; or brinzolamide and Triton X in milling bottle, and ball milling of the hot slurry after autoclaving, and then adding the slurry to the rest of the ingredients. It should be noted here that high temperatures and pressures of autoclave will dissolve brinzolamide. Later, when autoclaving is complete, upon cooling brinzolamide precipitates as large shaped crystals, having particle size of 1000 to 5000 µm. However, inclusion of tyloxapol and/or Triton X in the slurry allows the crystals to break up easily by ball milling. Brinzolamide cannot be administered as these large needle shaped crystals, as they will damage the eyes. Hence, precipitated brinzolamide crystals need to be milled to reduce their particle size.

Thus, the reference discloses autoclaving of the slurry of brinzolamide and surfactant and further ball milling the slurry. However, the drawback associated with this method is that it requires a milling bottle in which the slurry of brinzolamide could initially be autoclaved and then ball milled for further size reduction of needle shaped crystals of brinzolamide that are formed during autoclaving.

Dry heat sterilization causes melting of the material. Sterilization by ethylene oxide introduces unacceptable degradation products and residues, and sterilization by gamma irradiation of micronized material produces degradation products unacceptable for regulatory filing.

In most cases crystallization of active ingredients useful for ophthalmic use like carbonic anhydrase inhibitor, or others actives, occurs during preparation. Sterilization by autoclaving at temperature of 121° C. and 115 lbs of pressure leads to increase in solubility of the actives in the preparation and at that temperature brinzolamide goes into solution. However, upon cooling, brinzolamide precipitates as needle shaped crystals. These needle-shaped crystals are difficult to break and suspend. In different references either tyloxapol is used in solution so that the crystals are easier to break or special equipment such as ball mill and/or jet mill is used to break the large needle-shaped crystals.

The majority of the brinzolamide suspensions disclosed in the references faced the problem of crystallization and agglomeration of active ingredients during preparation as well as during storage. Crystallization or agglomeration of active leads to non-uniformity of dose, difficulty of administration, irritation to eye due to large drug particles and/or any ocular adverse effect due to high drug concentration.

So, there remains an unmet medical need to formulate a dosage form in which drugs like brinzolamide, but not limited to, having low solubility can be solubilized, to increase the permeability and bioavailability of the drug. None of the reference disclosed above teaches about increased solubility of brinzolamide or converting it in completely solution form.

Herein, the inventors of the present invention have surprisingly found that with the addition of the polymers such as Soluplus® and surfactants such as polysorbate 80 into the active ingredient brinzolamide to make the formulation completely dissolved in the solution form, the inventors of the present invention have surprisingly managed to reduce the concentration of brinzolamide solution, without effecting the safety and efficacy of the formulation.

The process of manufacturing of the ophthalmic formulation described herein is efficient, economic, and feasible for commercial scale preparation and in which the formulation does not require the use of specific equipment such as ball mill and/or jet mill as compared to the brinzolamide suspension known in the references.

Furthermore, the brinzolamide solution is easy to administer to the patients, the dosing variability's is also reduced as the general disadvantages of the suspension such as the settling of the drug particles, caking, agglomeration is not found in the brinzolamide solution of the present invention. Hence the formulation of the present invention is more patient compliant.

Thus, the objective of the present invention is to reduce the concentration of the active ingredient brinzolamide, wherein the active ingredient brinzolamide is in the solution form.

Another objective of the present invention is to provide an ophthalmic solution comprising brinzolamide alone or in combination with a second and/or a third IOP reducing and/or glaucoma treatment agents along with pharmaceutically acceptable ingredients(s) wherein the ophthalmic solution does not require the use of specific equipment such as ball mill and/or jet mill.

Herein, the inventors of the present invention have formulated a sterile, ophthalmic pharmaceutical formulation, wherein when the active ingredient with low aqueous solubility (such as CAIs such as but not limited to brinzolamide,) in combination with polymers like Soluplus® and a surfactant like polysorbate 80, is dissolved after heating above 50° C., the active ingredient brinzolamide does not precipitate and stays in solution form with the help of solubilizer Soluplus® and a surfactant like polysorbate 80.

The ophthalmic formulations of the present invention comprising a carbonic anhydrase inhibitor(s) (CAIs) such as latanoprost, travoprost, unoprostone, tafluprost, bimatoprost and the like, more specifically brinzolamide can also be used in combination with a second IOP reducing and/or glaucoma treatment agents, such as, but not limited to, beta-blockers, prostaglandin analogs, prostamides, alpha 2-adrenergic agonists, miotics, neuroprotectants and combinations thereof, wherein the ophthalmic formulations of the present invention is in the solution form.

The ophthalmic formulations of the present invention comprising a carbonic anhydrase inhibitor(s) (CAIs) such as latanoprost, travoprost, unoprostone, tafluprost, bimatoprost and the like, more specifically brinzolamide can also be used in combination with a third IOP reducing and/or glaucoma treatment agents, such as, but not limited to, beta-blockers, prostaglandin analogs, prostamides, alpha 2-adrenergic agonists, miotics, neuroprotectants and combinations thereof, wherein the ophthalmic formulations of the present invention is in the solution form.

The present invention provides an ophthalmic formulation comprising a pharmaceutically effective amount of brinzolamide in a solution form at about half of its current dose of 1.0%, preferably around 0.5% in combination with a second therapeutically active agent and its pharmacologically active metabolites, salts and racemates thereof or further in combination with third therapeutically active agent and its pharmacologically active metabolites, salts, solvates and racemates thereof wherein the ophthalmic formulation is in the solution form and a method of treating glaucoma and ocular hypertension and manufacturing process thereof.

SUMMARY OF THE INVENTION

The present invention relates to a sterile, ophthalmic pharmaceutical formulation in a solution form, comprising active ingredient(s) such as carbonic anhydrase inhibitors (CAIs) like brinzolamide in combination with a polymer like Soluplus® and a surfactant like polysorbate 80 and/or other pharmaceutically acceptable excipients.

The ophthalmic formulations of the present invention comprising a carbonic anhydrase inhibitor(s) (CAIS) such as latanoprost, travoprost, unoprostone, tafluprost, bimatoprost and the like, more specifically brinzolamide can also be used in combination with a second IOP reducing and/or glaucoma treatment agents, such as, but not limited to, beta-blockers, prostaglandin analogs, prostamides, carbonic anhydrase inhibitors (CAIs), alpha 2-adrenergic agonists, miotics, neuroprotectants and combinations thereof, wherein the ophthalmic formulations of the present invention is in the solution form.

The ophthalmic formulations of the present invention comprising a carbonic anhydrase inhibitor(s) (CAIs) such as latanoprost, travoprost, unoprostone, tafluprost, bimatoprost and the like, more specifically brinzolamide can also be used in combination with a third IOP reducing and/or glaucoma treatment agents, such as, but not limited to, beta-blockers, prostaglandin analogs, prostamides, alpha 2-adrenergic agonists, miotics, neuroprotectants and combinations thereof, wherein the ophthalmic formulations of the present invention is in the solution form.

The present invention relates to a sterile, ophthalmic pharmaceutical formulation comprising a combination of carbonic anhydrase inhibitors (CAIs) and prostaglandins and a polymer like Soluplus® along with other pharmaceutically acceptable excipients for the treatment of persons suffering from glaucoma and associated elevations of intraocular pressure (TOP) and/or ocular hypertension.

The present invention relates to a sterile, ophthalmic pharmaceutical formulation comprising a combination of carbonic anhydrase inhibitors (CAIs) and beta-blockers and a polymer like Soluplus® along with other pharmaceutically acceptable excipients for the treatment of persons suffering from glaucoma and associated elevations of intraocular pressure (IOP) and/or ocular hypertension.

The present invention provides an ophthalmic formulation comprising a pharmaceutically effective amount of brinzolamide in a solution form at about half of its current dose of 1.0%, preferably around 0.5% in combination with a second therapeutically active agent and its pharmacologically active metabolites, salts and racemates thereof or further in combination with third therapeutically active agent and its pharmacologically active metabolites, salts, solvates and racemates thereof wherein the ophthalmic formulation is in the solution form.

The present invention provides a method of treating glaucoma or ocular hypertension in a subject in need of such treatment, the method comprising administering to a subject in need thereof an ophthalmic formulation comprising a pharmaceutically effective amount of brinzolamide and its pharmacologically active salts thereof in combination with a second therapeutically active agent and its pharmacologically active metabolites, salts and racemates thereof or further in combination with third therapeutically active agent and its pharmacologically active metabolites, salts, solvates and racemates thereof wherein the ophthalmic formulation is in the solution form.

The present invention provides a process of manufacturing an ophthalmic formulation comprising a pharmaceutically effective amount of brinzolamide and its pharmacologically active salts thereof in combination with a second therapeutically active agent and its pharmacologically active metabolites, salts and racemates thereof or further in combination with third therapeutically active agent and its pharmacologically active metabolites, salts, solvates and racemates thereof wherein the ophthalmic formulation is in the solution form.

DETAILED DESCRIPTION OF THE INVENTION

As used herein, the term "second therapeutically active agent" is selected from, but not limited to, beta-blockers, prostaglandin analogs, prostamides, alpha 2-adrenergic agonists, miotics, neuroprotectants and combinations thereof.

As used herein, the term "third therapeutically active agent" is selected from, but not limited to, beta-blockers, prostaglandin analogs, prostamides, alpha 2-adrenergic agonists, miotics, neuroprotectants and combinations thereof.

As used herein, the terms "second therapeutically active agent" and "second intraocular pressure (IOP) reducing and/or glaucoma treatment agents" is interchangeably used.

As used herein, the terms "third therapeutically active agent" and "third intraocular pressure (IOP) reducing and/or glaucoma treatment agents" is interchangeably used.

As used herein, the term "treat" is to mean to relieve, reduce or alleviate at least one symptom of a disease in a subject. For example, the term "treat" may mean to reduce or alleviate elevated intraocular pressure and/or to reduce or prevent further damage or loss of retinal ganglion cells. For example, treatment can be diminishment of one or several symptoms of a disorder or complete eradication of a disorder.

As used herein, the term "topical application" as means application by way of a liquid, solution, suspension, gel, cream or ointment to the external corneal surface of a subject.

As used herein, the term "Soluplus®" wherever appears is an amphiphilic polyvinyl caprolactam-polyvinyl acetate-polyethylene glycol graft copolymer (PVCap-PVAc-PEG).

As used herein, the term "API" wherever appears is an abbreviation for "brinzolamide".

As used herein, the term "poorly soluble" when referring to a chemical compound in relation to its solubility in water or an oil, as defined in U.S. Pharmacopeia and National Formulary (USP-NF). According to this definition, solubility is stated in terms of the parts of the solvent needed to dissolve one part of the solute. A compound that is sparingly soluble in a particular solvent, such as water, requires 30-100 parts of the solvent to dissolve one part of the compound. A compound that is slightly soluble requires 100-1000 parts of the solvent. A compound that is very slightly soluble requires 1000-10,000 parts of the solvent. A compound that is insoluble requires more than 10,000 parts of the solvent to dissolve one part of the solute.

The present invention is to formulate a sterile, ophthalmic pharmaceutical formulation, wherein the poorly soluble drug/active ingredient such as carbonic anhydrase inhibitors (CAIs), solubilizes during either cooling after autoclaving or cooling after heating above 50° C. in highly solubilized form.

The present invention furthermore relates to the highly solubilized form of poorly insoluble drugs/active ingredient(s) to improve its bio-availability and manufacturability.

The present invention further relates to provide a process, wherein brinzolamide solution is formed by the use of ophthalmically acceptable ingredients such as polymers like Soluplus® {polyvinyl caprolactam-polyvinyl acetate-polyethylene glycol graft copolymer (PVCap-PVAc-PEG)} and surfactants like polysorbate 80 (Polyoxyethylene (20) sorbitan monooleate), in combination with a second and/or a third IOP reducing and/or glaucoma treatment agents along with pharmaceutically acceptable ingredients(s).

This present invention additionally provides a process for preparation of an ophthalmic formulation, wherein the inventors of the present invention have surprisingly managed to reduce the concentration of brinzolamide, without effecting the safety and efficacy of the formulation as compared to the concentration of brinzolamide present in suspension and the process described herein being efficient, economic, and feasible for commercial scale preparation and in which the formulation does not require the use of specific equipment such as ball mill and/or jet mill.

Further the invention provides a process which ameliorates one or more drawbacks of the reference cited processes.

In one embodiment, the second IOP reducing and/or glaucoma treatment agents is selected from the group comprising such as, but not limited to, beta-blockers, prostaglandin analogs, prostamides, alpha 2-adrenergic agonists, miotics, neuroprotectants, a parasympathomimetic drug, and combinations thereof.

In one embodiment, the second agent is a prostaglandin analog selected from, but not limited to, latanoprost, travoprost, unoprostone, tafluprost, bimatoprost and the like.

In one embodiment, the second agent is an alpha 2-receptor agonist selected from, but not limited to, brimonidine, apraclonidine and the like.

In one embodiment, the second agent is an alpha 1-receptor antagonist selected from, but not limited to, bunazosin and the like.

In one embodiment, the second agent is beta-receptor antagonist (beta-blockers) selected from, but not limited to, timolol, befunolol, carteolol, nipradilol, betaxolol, levobunolol, atenolol, metipranolol and the like.

In one embodiment, the second agent is neuroprotectants selected from, but not limited to, lubezole, nimodipine and the like.

In one embodiment, the second agent is a carbonic anhydrase inhibitor (CAIs) analog selected from, but not limited to, dorzolamide, brinzolamide, methazolamide, dichlorphenamide, diamox, acetazolamide and the like. In one embodiment, the second agent is a parasympathomimetic drug selected from, but not limited to, carbachol, echothiophate, pilocarpine and the like.

In one embodiment, the third IOP reducing and/or glaucoma treatment agents is selected from the group comprising such as, but not limited to, beta-blockers, prostaglandin analogs, prostamides, alpha 2-adrenergic agonists, miotics, neuroprotectants, a parasympathomimetic drug and combinations thereof.

In one embodiment, the third agent is a prostaglandin analog selected from, but not limited to, latanoprost, travoprost, unoprostone, tafluprost, bimatoprost and the like.

In one embodiment, the third agent is an alpha 2-receptor agonist selected from, but not limited to, brimonidine, apraclonidine and the like.

In one embodiment, the third agent is an alpha 1-receptor antagonist selected from, but not limited to, bunazosin and the like.

In one embodiment, the third agent is beta-receptor antagonist (beta-blockers) selected from, but not limited to, timolol, befunolol, carteolol, nipradilol, betaxolol, levobunolol, atenolol, metipranolol and the like.

In one embodiment, the third agent is neuroprotectants selected from, but not limited to, lubezole, nimodipine and the like.

In one embodiment, the third agent is a carbonic anhydrase inhibitor (CAIS) analog selected from, but not limited to, dorzolamide, brinzolamide, methazolamide, dichlorphenamide, diamox acetazolamide and the like.

In one embodiment, the third agent is a parasympathomimetic drug selected from, but not limited to, carbachol, echothiophate, pilocarpine and the like.

The concentration of the alpha 2-receptor agonist in an eye drop is not particularly limited, but, in the case of brimonidine, an eye drop containing brimonidine at a concentration of from 0.01 to 5 w/v %, preferably from 0.1 to 0.5 w/v %, more preferably 0.1 w/v %, 0.15 w/v %, 0.2 w/v % or 0.5 w/v % can be instilled once or several times per day. Further, in the case of apraclonidine, an eye drop containing apraclonidine at a concentration of from 0.01 to 5 w/v %, preferably from 0.5 to 1 w/v %, more preferably 0.5 w/v % or 1 w/v % can be instilled once or several times per day.

The concentration of the alpha 1-receptor antagonist in an eye drop is not particularly limited, but, in the case of bunazosin, an eye drop containing bunazosin at a concentration of from 0.001 to 0.3 w/v %, preferably from 0.003 to 0.03 w/v %, more preferably 0.01 w/v % can be instilled once or several times per day.

The concentration of the beta-receptor antagonist (beta-blockers) in an eye drop is not particularly limited, but, in the case of timolol, an eye drop containing timolol at a concentration of from 0.01 to 5 w/v %, preferably from 0.1 to 0.5 w/v %, more preferably 0.1 w/v %, 0.25 w/v % or 0.5 w/v % can be instilled once or several times per day. Further, in the case of befunolol, an eye drop containing befunolol at a concentration of from 0.01 to 5 w/v %, preferably from 0.25 to 1 w/v %, more preferably 0.25 w/v %, 0.5 w/v % or 1 w/v % can be instilled once or several times per day. In the case of carteolol, an eye drop containing carteolol at a concentration of from 0.01 to 5 w/v %, preferably from 1 to 2 w/v %, more preferably 1 w/v % or 2 w/v % can be instilled once or several times per day. In the case of nipradilol, an eye drop containing nipradilol at a concentration of from 0.01 to 5 w/v %, preferably 0.25 w/v % can be instilled once or several times per day. In the case of betaxolol, an eye drop containing betaxolol at a concentration of from 0.01 to 5 w/v %, preferably from 0.25 to 0.5 w/v %, more preferably 0.25 w/v % or 0.5 w/v % can be instilled once or several times per day. In the case of levobunolol, an eye drop containing levobunolol at a concentration of from 0.01 to 5 w/v %, preferably from 0.25 to 0.5 w/v %, more preferably 0.25 w/v % or 0.5 w/v % can be instilled once or several times per day. In the case of metipranolol, an eye drop containing metipranolol at a concentration of from 0.01 to 5 w/v %, preferably 0.3 w/v % can be instilled once or several times per day.

The concentration of the parasympathomimetic drug in an eye drop is not particularly limited, but, in the case of pilocarpine, an eye drop containing pilocarpine at a concentration of from 0.01 to 20 w/v %, preferably from 0.1 to 5 w/v %, more preferably 0.5 w/v %, 1 w/v %, 2 w/v %, 3 w/v % or 4 w/v % can be instilled once or several times per day.

The concentration of the carbonic anhydrase inhibitor (CAIs) in an eye drop is not particularly limited, but, in the case of dorzolamide, an eye drop containing dorzolamide at a concentration of from 0.01 to 5 w/v %, preferably from 0.5 to 2 w/v %, more preferably 0.5 w/v %, 1 w/v % or 2 w/v % can be instilled once or several times per day. Further, in the case of brinzolamide, an eye drop containing brinzolamide at a concentration of from 0.01 to 5 w/v %, preferably from 0.1 to 2 w/v %, more preferably 1 w/v % can be instilled once or several times per day. Further, in the case of acetazolamide, an eye drop containing acetazolamide at a concentration of from 0.01 to 5 w/v %, preferably from 1 to 5 w/v % can be used. Incidentally, in the case where acetazolamide is orally administered, a daily dose of from 250 to 1000 mg can be used.

The concentration of the prostaglandin in an eye drop is not particularly limited, but, in the case of latanoprost, an eye drop containing latanoprost at a concentration of from 0.0001 to 5 w/v %, preferably from 0.0005 to 1 w/v %, more preferably 0.001 to 0.1 w/v %, further more preferably 0.005 w/v % can be instilled once or several times per day. In the case of isopropyl unoprostone, an eye drop containing isopropyl unoprostone at a concentration of from 0.001 to 5 w/v %, preferably from 0.01 to 1 w/v %, more preferably 0.12 to 0.15 w/v %, further more preferably 0.12 w/v % or 0.15 w/v % can be instilled once or several times per day. In the case of bimatoprost, an eye drop containing bimatoprost at a concentration of from 0.0001 to 5 w/v %, preferably from 0.001 to 1 w/v %, more preferably 0.01 to 0.03 w/v %, further more preferably 0.01 w/v % or 0.03 w/v % can be instilled once or several times per day. In the case of travoprost, an eye drop containing travoprost at a concentration of from 0.0001 to 5 w/v %, preferably 0.001 to 1 w/v % more preferably 0.004 w/v % can be instilled once or several times per day.

The concentration of the Rho-kinase inhibitor in an eye drop is not particularly limited, but an eye drop containing the Rho-kinase inhibitor at a concentration of from 0.0001 to 5 w/v %, preferably from 0.001 to 1 w/v % can be instilled once or several times per day.

In any embodiment of the present invention, the preferred ophthalmic agents are carbonic anhydrase inhibitor (CAI) such as latanoprost, travoprost, unoprostone, tafluprost, bimatoprost and the like, more specifically brinzolamide or a combinations thereof, wherein the ophthalmic formulations of the present invention is in the solution form.

More preferably the ophthalmic agent is selected from the group comprising of brinzolamide and dorzolamide, or pharmaceutically acceptable salts thereof, in combination with beta-blockers or a pharmaceutically acceptable salt thereof (preferably timolol maleate), or in combination with prostaglandin analogs or a pharmaceutically acceptable salt thereof (preferably brimonidine tartrate) or in combination with alpha 2-adrenergic agonists.

Particularly preferred combination formulations of the present invention are carbonic anhydrase inhibitor (CAI) and prostaglandins or carbonic anhydrase inhibitor (CAI) and alpha 2-adrenergic agonists or carbonic anhydrase inhibitor (CAI) and prostamides or carbonic anhydrase inhibitor (CAI) and beta-blockers or carbonic anhydrase inhibitor (CAI) and parasympathomimetic.

More particularly preferred combination formulations of the present invention are carbonic anhydrase inhibitor (CAI) and prostaglandins and beta-blockers or carbonic anhydrase inhibitor (CAI) and alpha 2-adrenergic agonists and beta-blockers or carbonic anhydrase inhibitor (CAI) and prostamides and beta-blockers or carbonic anhydrase inhibitor (CAI) and parasympathomimetic and beta-blockers.

In a related embodiment, the methods as defined above further comprise the prior, simultaneous or sequential, application of a second and/or third ophthalmic agent.

In an embodiment, the present invention provides an ophthalmic formulation comprising a pharmaceutically effective amount of brinzolamide in a solution form at about half of its current dose of 1.0%, preferably around 0.5% in combination with a second therapeutically active agent and its pharmacologically active metabolites, salts and racemates thereof or further in combination with third therapeutically active agent and its pharmacologically active metabolites, salts, solvates and racemates thereof wherein the ophthalmic formulation is in the solution form.

In one of the embodiment, the present invention provides a method of treating glaucoma or ocular hypertension in a subject in need of such treatment, the method comprising administering to a subject in need thereof an ophthalmic formulation comprising a pharmaceutically effective amount of brinzolamide and its pharmacologically active salts thereof in combination with a second therapeutically active agent and its pharmacologically active metabolites, salts and racemates thereof or further in combination with third therapeutically active agent and its pharmacologically active metabolites, salts, solvates and racemates thereof wherein the ophthalmic formulation is in the solution form.

In another embodiment, the present invention provides a process of manufacturing an ophthalmic formulation comprising a pharmaceutically effective amount of brinzolamide and its pharmacologically active salts thereof in combination with a second therapeutically active agent and its pharmacologically active metabolites, salts and racemates thereof or further in combination with third therapeutically active agent and its pharmacologically active metabolites, salts, solvates and racemates thereof wherein the ophthalmic formulation is in the solution form.

In one of the embodiment, there is provided a process for preparing a composition suitable for preparing ophthalmic formulations as described herein comprising brinzolamide solution. The procedure is divided into four main steps:
1. Preparation of Remaining Product Vehicle (RPV)
2. Preparation of sterile Milli Q water
3. Preparation of solution containing API
4. Bulk preparation 1.0 Preparation of Remaining Product Vehicle (RPV)
1) Take 60% (of actual batch size) of milli Q water in a clean glass beaker.
2) Add slowly dispensed quantity of disodium edetate followed by mannitol under continuous stirring (rpm 800±100).
3) Slowly add dispensed quantity of carbomer into the above solution at increased rpm (2000±100) via sprinkling. Decrease the stirring rate to 1200±100 after complete addition.
4) After the carbomer has dissolved completely add dispensed quantity of sodium chloride under continuous stirring and stir till the solution is clear.
5) Check the initial pH of the solution, and adjust the pH to 7.5 with 5 N sodium hydroxide solution.
6) Make up the volume with milli Q water upto 80% (of actual batch size).
7) Filter the bulk solution through 47 mm, 20 micron PP filters.
8) Autoclave the RPV at 121° C. for 30 min in a Schott glass bottle.

Note: About 10% RPV excess is prepared to compensate the loss of RPV during filtration and autoclaving. Please note the formulation is stating the exact quantities. However, dispensed quantities will be in 10% excess.

2.0 Preparation of Sterile Milli Q Water
1) In a Schott glass bottle autoclave enough water that will comprise 20% of total weight of the product. This can be autoclaved in a separate bottle, while autoclaving RPV. Autoclaving to be done at 121° C. for 30 min.

3.0 Preparation of Solution Containing API
1) Take 10% (of actual batch size) of 0.25% tyloxapol solution (if required in formulation, otherwise simply use water) added in a clean glass beaker.
2) Add slowly dispensed quantity of Polysorbate 80 followed by soluplus to it under stirring.
3) Add slowly dispensed quantity of Benzalkonium chloride to the above solution under continuous stirring and stir till the solution is clear.
4) Add slowly dispensed quantity of API (brinzolamide, followed by Latanoprost) to it under continuous stirring.
5) Decrease the pH of the slurry to approximately 3.5 with 5 N hydrochloric acid till the API dissolves completely.
6) Make up the volume of the solution to 20% of the bulk solution and adjust the pH of the solution to 6.0 with 5 N sodium hydroxide
7) Filter through 47 mm, 0.45 micron PVDF filter followed by 47 mm, 0.22 micron PVDF filter into a large sterile container under laminar flow hood.

4.0 Bulk Preparation
1) To the above prepared sterile API solution which is 20% of the bulk solution, add previously autoclaved RPV to make up the weight to 90%. That is addition of about 70% of the RPV by weight.
2) Make up the volume with previously sterilized milli Q water upto 100.0% (of actual batch size)
3) Stir the solution for 2 hours in aseptic conditions.
4) Fill the final solution in previously sterilized bottles, suitable for ophthalmic use.

As used herein, a "combination of agents" and similar terms refer to a combination of two types of agents: (1) carbonic anhydrase inhibitors and/or pharmacologically active metabolites, salts, solvates and racemates of CAIs agents and (2) prostaglandin analogs and/or pharmacologically active metabolites, salts, solvates and racemates of prostaglandin analogs.

As used herein, a "combination of agents" and similar terms refer to a combination of three types of agents: (1) carbonic anhydrase inhibitors and/or pharmacologically active metabolites, salts, solvates and racemates of CAIs agents and (2) prostaglandin analogs and/or pharmacologically active metabolites, salts, solvates and racemates of prostaglandin analogs and (3) beta-blockers and/or pharmacologically active metabolites, salts, solvates and racemates of prostaglandin analogs.

Pharmacologically active metabolites include those that are inactive but are converted into pharmacologically active forms in the body after administration.

Administration of the combination includes administration of the combination in a single formulation or unit dosage form, administration of the individual agents of the combination concurrently but separately, or administration of the individual agents of the combination sequentially by any suitable route.

The dosage of the individual agents of the combination may require more frequent administration of one of the agents as compared to the other agent in the combination. Therefore, to permit appropriate dosing, packaged pharmaceutical products may contain one or more dosage forms that contain the combination of agents, and one or more dosage forms that contain one of the combinations of agents, but not the other agent(s) of the combination.

The optimal dose of the combination of agents use in the methods described herein can be determined empirically for each individual using known methods and will depend upon a variety of factors, including, though not limited to, the degree of advancement of the disease; the age, body weight, general health, gender and diet of the individual; the time of administration; and other medications the individual is taking. Optimal dosages may be established using routine testing and procedures that are well known in the art.

Frequency of dosage may vary depending on the formulation used and the particular condition to be treated or prevented and the patient's/subject's medical history. In general, the use of the minimum dosage that is sufficient to provide effective therapy is preferred. Patients may generally be monitored for therapeutic effectiveness using assays or tests suitable for monitoring IOP or retinal damage for the condition being treated or prevented, which will be familiar to those of ordinary skill in the art.

In one embodiment, the prostaglandin include prostaglandins disclosed in JP-A-59-1418 (particularly, a natural prostaglandin such as prostaglandin F2 alpha), prostaglandins such as latanoprost disclosed in JP-T-3-501025, prostaglandins such as isopropyl unoprostone disclosed in JP-A-2-108, prostaglandins such as bimatoprost disclosed in JP-T-8-501310, prostaglandins such as travoprost disclosed in JP-A-10-182465, prostaglandins such as AL-6598 disclosed in Sury Opthalmol 47 (Suppl 1): S13-S33, 2002, and prostaglandins such as PF-04475270 disclosed in Exp Eye Res. 89: 608-17, 2009. Among these, the prostaglandin is preferably PGF2alpha or a PGF2 alpha derivative, more preferably isopropyl unoprostone, latanoprost, travoprost or bimatoprost.

In one embodiment, the alpha 2-receptor agonist includes brimonidine and apraclonidine.

In one embodiment, the alpha 1-receptor antagonist includes bunazosin.

In one embodiment, the beta-receptor antagonist include timolol, befunolol, carteolol, nipradilol, betaxolol, levobunolol and metipranolol.

In one embodiment, the carbonic anhydrase inhibitor includes dorzolamide, brinzolamide and acetazolamide.

According to one embodiment of the present invention, there is provided a sterile ophthalmic formulation prepared by the process as described herein comprising brinzolamide in an amount from 0.01% to 5.0% by weight.

In preferred embodiments, the present invention provides sterile ophthalmic formulations in the form of aqueous liquids, solutions, emulsion, solid dispersion, suspension, reverse emulsion and microemulsion, nanoemulsion, liposomes, nano reservoir system, in-situ gel drops, nanoparticulate system, liposomal drops, bioadhesive gel drops, drops and the like.

In another preferred embodiment, the present invention provides ophthalmic formulations for topical ophthalmic delivery comprising administering said composition in the eyes. Other preferred embodiments include otic and/or nasal formulations for administration to the ear and/or nose of a human or animal.

In a more preferred embodiment of the present invention, the pharmaceutically acceptable excipients are selected from but not limited to at least one polymer, at least one surfactant, at least one isotonicity agent, at least one viscosity enhancing agent, at least one solvent, at least one buffer, at least one pH adjusting agents, at least one antioxidants, at least one chelating agents and at least one preservative.

In one of the embodiments, the polymers that may be used is selected from the group consisted of, but are not limited to Carbomer® such as Carbomer 974 P, Soluplus® (polyvinyl caprolactam-polyvinyl acetate-polyethylene glycol graft copolymer), povidone, hydroxypropylmethylcellulose, hydroxypropylcellulose, hydroxyethylcellulose and mixtures thereof, wherein the said polymers may be used in amount from 0.01% to 5.0%.

In one of the embodiments, the preservatives that may be used is selected from the group consisted of, but are not limited to benzethonium chloride, phenyl ethanol, phenyl propanol, phenyl mercuric acetate, phenyl mercuric nitrate, phenyl mercuric borate, chlorhexidine acetate or gluconate, cetrimide, chlorocresol, benzoic acid, benzyl alcohol, butylparaben, propylparaben, methylparaben, chlorobutanol, phenoxyethanol, sodium methyl paraben, sodium propyl paraben, thimerosal, benzalkonium chloride, hydrogen peroxide, sodium chlorite and mixtures thereof, wherein the said preservatives may be used in an amount from 0.005% to 0.5%.

In another embodiment, the surfactants that may be used is selected from the group consisted of, but are not limited to sodium lauryl sulfate, docusate sodium, polyoxyalkyl ethers, polyoxylalkyl phenyl ethers, polyoxyl 40 hydrogenated castor oil (Cremophor RH 40), polyoxyl 40 stearates, polyoxy hydrogenated castor oil, polyoxy sorbitan esters, sorbitan esters, polysorbates, polyoxyl 35 castor oil, sorbitan monolaureates, poloxamer and mixtures thereof, wherein the said surfactants may be used in amount from 0.001% to 15%, preferably 0.01% to 0.5%.

In another embodiment, the nonionic surfactant that may be used is selected from the group consisted of, but are not limited to tyloxapol; polyoxyethylene sorbitan esters, such as polysorbate 20, polysorbate 60, and polysorbate 80; polyethoxylated castor oils, such as Cremaphor EL; polyethoxylated hydrogenated castor oils, such as HCO-40; and poloxamers. wherein the said surfactants may be used in amount from about 0.01-0.2%.

In one of the embodiments, the tonicity agents that may be used is selected from the group consisted of, but are not limited to mannitol, dextrose, glycerin, potassium chloride, sodium chloride and mixtures thereof, wherein the tonicity agents may be used in amount from about 0.1% to 5.0% or is added in such an amount that makes the osmotic pressure of the composition identical to that of tears.

In other embodiments, the solvent, preferably a polar organic solvent, is selected from the group consisting of, but not limited to N-methyl pyrrolidinone, aliphatic and aromatic alcohols, ethanol, dimethyl sulfoxide (DMSO), dimethyl acetamide, ethoxydiglycol, isopropyl myristate, triacetin, polyethylene glycols, and propylene glycol.

In another embodiment, the viscosities enhancing agents that may be used is selected from the group comprising of, but are not limited to, carboxymethylcellulose sodium, hydroxyethyl cellulose, hydroxypropyl cellulose, hydroxymethyl cellulose, hydroxypropyl methylcellulose, methylcellulose carbomer, poloxamer, polyvinyl alcohol, povidone, polyethylene oxide, carboxymethylcellulose calcium.

In another embodiment of the present invention, the buffers include acetates such as sodium acetate; phosphates such as sodium dihydrogenphosphate, disodium hydrogenphosphate, potassium dihydrogenphosphate and dipotassium hydrogenphosphate; ε-aminocaproic acid; amino acid salts such as sodium glutamate; and boric acid and a salt thereof, wherein the buffer is generally contained in a proportion of 0.01 to 2.0 w/v % relative to the entire composition.

In another embodiment of the present invention, the buffer should have buffering capacity in the range of pH 4.5-8.5.

In one of another embodiment of the present invention, the pH adjusting agent include but are not limited to, hydrochloric acid, citric acid, phosphoric acid, acetic acid, tartaric acid, sodium hydroxide, potassium hydroxide, sodium carbonate and sodium hydrogencarbonate.

In one of another embodiment of the present invention, the chelating agents include but are not limited to edetate disodium, edetate trisodium, edetate tetrasodium, diethyleneamine pentaacetate and mixtures thereof, wherein the chelating agent is generally present in an amount from 0.005-0.2 w/v % relative to the entire composition.

In one of another embodiment of the present invention, the antioxidants include but are not limited to sodium bisulfite, potassium bisulfite, magnesium bisulfite, calcium bisulfite, sodium metabisulfite, potassium metabisulfite, calcium metabisulfite, sodium thiosulfate and sodium hydrogensulfite, ascorbic acid, sodium ascorbate, tocopherol and sulfite salts like sodium sulfite, potassium sulfite, magnesium sulfite, calcium sulfite, wherein the sulfite salt is generally being present in an amount from 0.01-1.0% w/v.

In one of another embodiment of the present invention, the sterile, ophthalmic pharmaceutical formulation may be aseptically sterilized using membrane filters such as PES (Polyethersulphone), PVDF (Polyvinylidene Fluoride) having pore size of about 0.45 microns to 0.22 microns to filter the formulation vehicle. In another embodiment of the present invention, the ophthalmic formulation of brinzolamide prepared according to the process as described herein may be filled in LDPE or HDPE or PET or polycarbonate vials of suitable capacity in volumes of 0.5 to 20 mL.

Another embodiment of the present invention consists of the active ingredient which is useful in the treatment or prevention of diseases associated with the eye(s) like elevated intraocular pressure in patients with ocular hypertension or open-angle glaucoma, ocular surface pain, uveitis, scleritis, episcleritis, keratitis, surgically-induced inflammation, endophthalmitis, iritis, atrophic macular degeneration, retinitis pigmentosa, iatrogenic retinopathy, retinal tears, retinal vein and artery occlusion, optic neuropathy, neovascular glaucoma, corneal neovascularization, cyclitis, sickle cell retinopathy, pterygium, seasonal allergic conjunctivitis, palpebral and bulbar conjunctiva, acne rosacea, superficial punctuate keratitis, herpes zoster keratitis, iritis, cyclitis, selected infective conjunctivitides, and post-operative inflammation following ocular surgery.

Accordingly, the main embodiment of the present invention provides an aqueous sterile, ophthalmic pharmaceutical formulation for lowering intraocular pressure in a patient suffering from elevated intraocular pressure comprising a carbonic anhydrase inhibitor or its pharmaceutically acceptable salt as an active agent and a polymer and a second or, third therapeutically active agent optionally along with pharmaceutically acceptable excipients and/or mixtures thereof, wherein the formulation is in solution form.

In another embodiment of the present invention, the carbonic anhydrase inhibitor is selected from a group, but not limited to, brinzolamide, dorzolamide, acetazolamide and/or, mixtures thereof.

In another embodiment of the present invention, the carbonic anhydrase inhibitor is brinzolamide.

In another embodiment of the present invention, the brinzolamide is present in amount from 0.01 to 5 w/v % of the formulation.

In another embodiment of the present invention, the brinzolamide is present in amount from 0.1 to 2 w/v % of the formulation.

In another embodiment of the present invention, the brinzolamide is present in amount from 0.3 to 1.0% of the formulation.

In another embodiment of the present invention, the second therapeutically active agent is selected from a group comprising (i) beta-blockers (ii) prostaglandin analogs, (iii) prostamides, (iv) alpha 2-adrenergic agonists, (v) miotics, (vi) neuroprotectants, (vii) parasympathomimetic drug, or, their pharmacologically active metabolites, salts and racemates and/or mixtures thereof.

In another embodiment of the present invention, the second therapeutically active agent is selected from a group comprising latanoprost, travoprost, unoprostone, tafluprost, bimatoprost, brimonidine, apraclonidine, bunazosin, timolol, befunolol, carteolol, nipradilol, betaxolol, levobunolol, atenolol, metipranolol, lubezole, nimodipine, carbachol, echothiophate, pilocarpine and/or, mixtures thereof.

In another embodiment of the present invention, the second therapeutically active agent is timolol.

In another embodiment of the present invention, the third therapeutically active agent, is selected from a group comprising (i) beta-blockers, (ii) prostaglandin analogs, (iii) prostamides, (iv) alpha 2-adrenergic agonists, (v) miotics, (vi) neuroprotectants, (vi) parasympathomimetic drug or, their pharmacologically active metabolites, salts, racemates and/or mixtures thereof.

In another embodiment of the present invention, the third therapeutically active agent is selected from a group comprising latanoprost, travoprost, unoprostone, tafluprost, bimatoprost, brimonidine, apraclonidine, bunazosin, timolol, befunolol, carteolol, nipradilol, betaxolol, levobunolol, atenolol, metipranolol, lubezole, nimodipine, dorzolamide, brinzolamide, methazolamide, dichlorphenamide, diamox acetazolamide, carbachol, echothiophate, pilocarpine and/or mixtures thereof, In another embodiment of the present invention, the third therapeutically active agent is latanoprost.

In another embodiment of the present invention, the polymer is selected from a group comprising Carbomer 974 P (Carbomer®), polyvinyl caprolactam-polyvinyl acetate-polyethylene glycol graft copolymer (Soluplus®), povidone, hydroxypropylmethylcellulose, hydroxypropylcellulose, hydroxyethylcellulose and/or mixtures thereof.

In another embodiment of the present invention, the polymer is polyvinyl caprolactam-polyvinyl acetate-polyethylene glycol graft copolymer.

In another embodiment of the present invention, the polymer is present in amount from 0.01% to 5.0% by weight of the formulation.

In another embodiment of the present invention, the polymer is present in amount from 0.1 to 3.0% by weight of the formulation.

In another embodiment of the present invention, the polymer is present in amount from 0.3 to 1.0% by weight of the formulation.

In another embodiment of the present invention, the formulation further comprising a surfactant selected from a group comprising sodium lauryl sulfate, docusate sodium, polyoxyalkyl ethers, polyoxylalkyl phenyl ethers, polyoxyl 40 hydrogenated castor oil (Cremophor RH 40), polyoxyl 40 stearates, polyoxy hydrogenated castor oil, polyoxy sorbitan esters, sorbitan esters, polysorbates, polyoxyl 35 castor oil, sorbitan monolaureates, poloxamer and/or mixtures thereof.

In another embodiment of the present invention, the surfactant is polysorbate, preferably polysorbate 80.

In another embodiment of the present invention, the surfactant is present in amount from 0.001% to 15% by weight of the formulation.

In another embodiment of the present invention, the surfactant is present in amount from 0.01 to 5.0% by weight of the formulation.

In another embodiment of the present invention, the surfactant is present in amount from 0.05 to 3.0% by weight of the formulation.

In another embodiment of the present invention, the pharmaceutically acceptable excipients are selected from group comprising a tonicity agent, a viscosity enhancing agent, a non-aqueous solvent, a buffer, a pH adjusting agent, an antioxidant, a chelating agent, a preservative, and/or a combination of two or more thereof.

In another embodiment of the present invention, the formulation is in the form of aqueous liquids, solutions, emulsion, solid dispersion, suspension, reverse emulsion and microemulsion, nanoemulsion, liposomes, nano reservoir system, in-situ gel drops, nanoparticulate system, liposomal drops, bioadhesive gel drops, drops.

In another embodiment of the present invention, the formulation comprises brinzolamide, polyvinyl caprolactam-polyvinyl acetate-polyethylene glycol graft copolymer, polysorbate 80 and either a second or third therapeutically active agent and pharmaceutically acceptable excipients and/or mixtures thereof.

In another embodiment of the present invention, the formulation comprises brinzolamide, polyvinyl caprolactam-polyvinyl acetate-polyethylene glycol graft copolymer, polysorbate 80 and latanoprost as second therapeutically active agent and pharmaceutically acceptable excipients and/or mixtures thereof.

In another embodiment of the present invention, the formulation comprises brinzolamide, polyvinyl caprolactam-polyvinyl acetate-polyethylene glycol graft copolymer, polysorbate 80 and timolol as third therapeutically active agent and pharmaceutically acceptable excipients and/or mixtures thereof.

In another embodiment of the present invention, the formulation has application in the treatment of elevated intraocular pressure in patients with glaucoma or ocular hypertension.

Yet another embodiment of the present invention provides a method of treating elevated intraocular pressure in patients with glaucoma or ocular hypertension in a subject in need of such treatment, the method comprising administering to a subject in need thereof an ophthalmic formulation containing a pharmaceutically effective amount of brinzolamide or, its salts thereof and optionally in combination with a second or third therapeutically active agent and its pharmacologically active metabolites, salts or, racemates thereof and/or pharmaceutically acceptable excipients.

In another embodiment of the present invention, the formulation is administered once a day to each eye in need thereof.

In another embodiment of the present invention, the formulation is administered twice or three times a day to each eye in need thereof.

In another embodiment of the present invention, the condition treatable includes elevated intraocular pressure.

In another embodiment of the present invention, the formulation pH ranges from 5.5 to 8.

EXAMPLES

The scope of the present invention is illustrated by the following examples which are not meant to restrict the scope of the invention in any manner whatsoever.

The term 'q.s.' wherever appears in the examples is an abbreviation for 'quantity sufficient' which is the amount of the excipient in such quantities that is just sufficient for its use in the composition of the present invention.

Various exemplary embodiments can be formulated as shown in the table follows:

| Ingredients | Quantity (% w/v) |
| --- | --- |
| Active pharmaceutical ingredient (API) | 0.001-5 |
| Graft co-polymer | 0.01-3 |
| Surfactant | 0.05-5 |
| Wetting agent | 0-2 |
| Chelating agent. | 0.001-2 |
| Osmotic agent | 0.5-20 |
| Viscosity modifier | 0.01-5 |
| Osmotic agent | 0-10 |
| Preservatives | 0-0.1 |
| pH adjusting agent. | q.s. to adjust pH to 4.5-7.5 |
| pH adjusting agent. | q.s. to adjust pH to 4.5-7.5 |
| Purified water | q.s. to 100 mL |

The scope of the present invention is illustrated by the following examples which are not meant to restrict the scope of the invention in any manner whatsoever.

Formula 1:

| Ingredient | Quantity (% w/w) |
| --- | --- |
| Brinzolamide | 0.3-0.5 |
| Soluplus | 0.4-0.8 |
| Polysorbate - 80 | 1.0 |
| Tylaxapol | 0.0-0.05 |
| Edetate disodium | 0.01 |
| Mannitol | 3.3 |
| Carbomer | 0.4-0.45 |
| NaCl | 0.19 |
| Benzalkonium Chloride | 0.0-0.01 |
| NaOH | q.s. to adjust pH to 6.0 |
| HCl | q.s. to adjust pH to 6.0 |
| Milli Q | q.s. to 100 mL |

Method of Preparation:

The manufacturing process is as follows: The procedure is divided into four main steps
1. Preparation of Remaining Product Vehicle (RPV)
2. Preparation of sterile Milli Q water
3. Preparation of solution containing API
4. Bulk preparation 1.0 Preparation of Remaining Product Vehicle (RPV)
 1) Take 60% (of actual batch size) of milli Q water in a clean glass beaker.
 2) Add slowly dispensed quantity of disodium edetate followed by mannitol under continuous stirring (rpm 800±100).
 3) Slowly add dispensed quantity of carbomer into the above solution at increased rpm (2000±100) via sprinkling. Decrease the stirring rate to 1200±100 after complete addition.
 4) After the carbomer has dissolved completely add dispensed quantity of sodium chloride under continuous stirring and stir till the solution is clear.

5) Add slowly dispensed quantity of Benzalkonium chloride to the above solution under continuous stirring and stir till the solution is clear.
6) Check the initial pH of the solution, and adjust the pH to 7.5 with 5 N sodium hydroxide solution.
7) Make up the volume with milli Q water upto 80% (of actual batch size).
8) Filter the bulk solution through 47 mm, 20 micron PP filters.
9) Autoclave the RPV at 121° C. for 30 min in a Schott glass bottle.
Note: About 10% RPV excess is prepared to compensate the loss of RPV during filtration and autoclaving. Please note the formulation is stating the exact quantities. However, dispensed quantities will be in 10% excess.

2.0 Preparation of Sterile Milli Q Water

1) In a Schott glass bottle autoclave enough water that will comprise 20% of total weight of the product. This can be autoclaved in a separate bottle, while autoclaving RPV. Autoclaving to be done at 121° C. for 30 min.

3.0 Preparation of Solution Containing API

1) Take 10% (of actual batch size) of 0.25% tyloxapol solution (if required in formulation, otherwise simply use water) added in a clean glass beaker.
2) Add slowly dispensed quantity of Polysorbate 80 followed by soluplus to it under stirring.
3) Add slowly dispensed quantity of API to it under continuous stirring.
4) Decrease the pH of the slurry to approximately 3.5 with 5 N hydrochloric acid till the API dissolves completely.
5) Make up the volume of the solution to 20% of the bulk solution and adjust the pH of the solution to 6.0 with 5 N sodium hydroxide.
6) Filter through 47 mm, 0.45 micron PVDF filter followed by 47 mm, 0.22 micron PVDF filter into a large sterile container under laminar flow hood.

1.1 Bulk Preparation

1) To the above prepared sterile API solution which is 20% of the bulk solution, add previously autoclaved RPV to make up the weight to 90%. That is addition of about 70% of the RPV by weight.
2) Make up the volume with previously sterilized milli Q water upto 100.0% (of actual batch size)
3) Stir the solution for 2 hours in aseptic conditions.
4) Fill the final solution in previously sterilized bottles, suitable for ophthalmic use.

Formula 2:

| Ingredient | Quantity (% w/w) |
|---|---|
| Brinzolamide | 0.3-0.5 |
| Latanoprost | 0.005 |
| Soluplus | 0.4-0.8 |
| Polysorbate - 80 | 1.0 |
| Tylaxapol | 0.0-0.05 |
| Edetate disodium | 0.01 |
| Mannitol | 3.3 |
| Carbomer | 0.4-0.45 |
| NaCl | 0.19 |
| Benzalkonium Chloride | 0.0-0.01 |
| NaOH | q.s. to adjust pH to 6.0 |
| HCl | q.s. to adjust pH to 6.0 |
| Milli Q | q.s. to 100 mL |

Method of Preparation:

The manufacturing process is as follows: The procedure is divided into four main steps 1. Preparation of Remaining Product Vehicle (RPV)
2. Preparation of sterile Milli Q water
3. Preparation of solution containing API
4. Bulk preparation 1.0 Preparation of Remaining Product Vehicle (RPV)

1) Take 60% (of actual batch size) of milli Q water in a clean glass beaker.
2) Add slowly dispensed quantity of disodium edetate followed by mannitol under continuous stirring (rpm 800±100).
3) Slowly add dispensed quantity of carbomer into the above solution at increased rpm (2000±100) via sprinkling. Decrease the stirring rate to 1200+100 after complete addition.
4) After the carbomer has dissolved completely add dispensed quantity of sodium chloride under continuous stirring and stir till the solution is clear.
5) Check the initial pH of the solution, and adjust the pH to 7.5 with 5 N sodium hydroxide solution.
6) Make up the volume with milli Q water upto 80% (of actual batch size).
7) Filter the bulk solution through 47 mm, 20 micron PP filters.
8) Autoclave the RPV at 121° C. for 30 min in a Schott glass bottle.

Note: About 10% RPV excess is prepared to compensate the loss of RPV during filtration and autoclaving. Please note the formulation is stating the exact quantities. However, dispensed quantities will be in 10% excess.

2.0 Preparation of Sterile milli Q water

1) In a Schott glass bottle autoclave enough water that will comprise 20% of total weight of the product. This can be autoclaved in a separate bottle, while autoclaving RPV. Autoclaving to be done at 121° C. for 30 min.

3.0 Preparation of solution containing API

1) Take 10% (of actual batch size) of 0.25% tyloxapol solution (if required in formulation, otherwise simply use water) added in a clean glass beaker.
2) Add slowly dispensed quantity of Polysorbate 80 followed by soluplus to it under stirring.
3) Add slowly dispensed quantity of Benzalkonium chloride to the above solution under continuous stirring and stir till the solution is clear.
4) Add slowly dispensed quantity of API (brinzolamide, followed by Latanoprost) to it under continuous stirring.
5) Decrease the pH of the slurry to approximately 3.5 with 5 N hydrochloric acid till the API dissolves completely.
6) Make up the volume of the solution to 20% of the bulk solution and adjust the pH of the solution to 6.0 with 5 N sodium hydroxide
7) Filter through 47 mm, 0.45 micron PVDF filter followed by 47 mm, 0.22 micron PVDF filter into a large sterile container under laminar flow hood.

4.0 Bulk Preparation

1) To the above prepared sterile API solution which is 20% of the bulk solution, add previously autoclaved RPV to make up the weight to 90%. That is addition of about 70% of the RPV by weight.
2) Make up the volume with previously sterilized milli Q water upto 100.0% (of actual batch size)
3) Stir the solution for 2 hours in aseptic conditions.
4) Fill the final solution in previously sterilized bottles, suitable for ophthalmic use.

Formula 3:

| Ingredients | Quantity (% w/w) |
| --- | --- |
| Brinzolamide | 0.5 |
| Timolol maleate (equivalent to 0.5% timolol) | 0.683 |
| Soluplus | 0.8 |
| Polysorbate - 80 | 1 |
| Edetate disodium | 0.01 |
| Mannitol | 3 |
| Carbomer | 0.42 |
| NaCl | 0.1 |
| Benzalkonium Chloride (50%) | 0.02 |
| NaOH | q.s. to adjust pH to 6.0 |
| HCl | q.s. to adjust pH to 6.0 |
| Milli Q | q.s. to 100 mL |

Method of Preparation:

The manufacturing process is as follows: The procedure is divided into four main steps 1.0 Preparation of Remaining Product Vehicle (RPV)
  1) Take 60% (of actual batch size) of milli Q water in a clean glass beaker.
  2) Add slowly dispensed quantity of disodium edetate followed by mannitol under continuous stirring (rpm 800±100).
  3) Slowly add dispensed quantity of carbomer into the above solution at increased rpm (2000±100) via sprinkling. Decrease the stirring rate to 1200±100 after complete addition.
  4) After the carbomer has dissolved completely add dispensed quantity of sodium chloride under continuous stirring and stir till the solution is clear.
  5) Add slowly dispensed quantity of Benzalkonium chloride to the above solution under continuous stirring and stir till the solution is clear.
  6) Check the initial pH of the solution, and adjust the pH to 6.0 with 5 N sodium hydroxide solution.
  7) Make up the volume with milli Q water upto 80% (of actual batch size).
  8) Filter the bulk solution through 47 mm, 20 micron PP filters.
  9) Autoclave the RPV at 121° C. for 30 min in a Schott glass bottle.
     Note: About 10% RPV excess is prepared to compensate the loss of RPV during filtration and autoclaving. Please note the formulation is stating the exact quantities. However, dispensed quantities will be in 10% excess.

2.0 Preparation of Sterile Milli Q Water
  1) In a Schott glass bottle autoclave enough water that will comprise 20% of total weight of the product. This can be autoclaved in a separate bottle, while autoclaving RPV. Autoclaving to be done at 121° C. for 30 min.

3.0 Preparation of Solution Containing API
  1) Take 10% (of actual batch size) of Sterile Milli Q water in a clean glass beaker.
  2) Add slowly dispensed quantity of Polysorbate 80 followed by soluplus to it under stirring.
  3) Add slowly dispensed quantity of API (timolol followed by brinzolamide) to it under continuous stirring.
  4) Decrease the pH of the slurry to approximately 3.5 with 5 N hydrochloric acid till the API dissolves completely.
  5) Make up the volume of the solution to 20% of the bulk solution and adjust the pH to 6.0 with 5 N sodium hydroxide
  6) Filter through 47 mm, 0.45 micron PVDF filter followed by 47 mm, 0.22 micron PVDF filter into a large sterile container under laminar flow hood.

4.0 Bulk Preparation
  1) To the above prepared sterile API solution which is 20% of the bulk solution, add previously autoclaved RPV to make up the weight to 90%. That is addition of about 70% of the RPV by weight.
  2) Make up the volume with previously sterilized milli Q water upto 100.0% (of actual batch size)
  3) Stir the solution for 2 hours in aseptic conditions.
  4) Fill the final solution in previously sterilized bottles, suitable for ophthalmic use.

Formula 4:

| Ingredients | Quantity (% w/w) |
| --- | --- |
| Brinzolamide | 0.50 |
| Timolol maleate (equivalent to 0.5% timolol) | 0.683 |
| Soluplus | 0.80 |
| Polysorbate - 80 | 1.00 |
| Mannitol | 2.50 |
| Carbomer | 0.42 |
| Boric Acid | 0.188 |
| Sodium Borate | 0.012 |
| Zinc Chloride | 0.10 |
| Benzalkonium Chloride (50%) | 0.01 |
| Sodium metabisulphite | 0.20 |
| NaOH | q.s. to adjust pH to 6.0 |
| HCl | q.s. to adjust pH to 6.0 |
| Milli Q | q.s. to 100 mL |

Stability Studies:

A sterile, ophthalmic pharmaceutical formulation of the present invention is prepared by the process described herein in the specification and is tested for stability at stress conditions for 4 weeks at 50° C. and at accelerated conditions for one month at 40° C., at not more than 25% relative humidity (RH). The results of the same are provided in Table 1.

An accelerated study comprises placing the formulation is filled in 10 mL 3 piece opaque LDPE bottles, opaque LDPE nozzle and orange colored cap. (Sterilized by ETO gas Sterilization) and maintaining at 40° C., at not more than 25% relative humidity (RH) in the dark.

As understood by those of skill in the art, when the drug comprises brinzolamide, the impurities preferably measured include Impurity A (S)-4-(ethylamino)-3,4-dihydro-2-(3-methoxypropyl)-2H-thieno[3,2-e]-1,2-thiazine-6-sulfonamide 1,1-dioxide; Impurity B, (R)-4-(amino)-3,4-dihydro-2-(3-methoxypropyl)-2H-thieno[3,2-e]-1,2-thiazine-6-sulfonamide 1,1-dioxide, Impurity C (S)-4-(hydroxy)-3,4-dihydro-2-(3-methoxypropyl)-2H-thieno[3,2-e]-1,2-thiazine-6-sulfonamide 1,1-dioxide and Impurity D 6-(amino-hydroxy-oxo-6-sulfanyl)-2-(3-methoxypropyl)-1,1-dioxo-3H-thieno[3,2-e]thiazin-4-one and total impurities, as well as identification of the amount of the any independent unspecified impurity.

As understood by those of skill in the art, when the drug comprises timolol, the impurities preferably measured include Impurity-1 3-Chloro-4(N-Morpholino-1,2,5-thiadazole), and total impurities, as well as identification of the amount of the any independent unspecified impurity.

TABLE 1

Stability data of brinzolamide and timolol formulation (Formula 3) as prepared by process disclosed herein the specification at stress (4 Week/50° C.) and accelerated (1 Month/(40° C./NMT 25% RH)) stability condition.

| Parameters | Specification | Initial | 2 Week/ 50° C. | 4 Week/ 50° C. | 1 Month/ (40° C./ NMT 25% RH) |
|---|---|---|---|---|---|
| Description | Not specified | White opalescent viscous solution | | | |
| Assay of Brinzolamide | 90%-110% | 99.60% | 99.50% | 100.10% | 100.00% |
| Impurity of Brinzolamide | | | | | |
| Impurity A | NMT 2.0% | ND | 0.57% | 0.92% | 0.26% |
| Impurity B | NMT 0.5% | 0.11% | 0.07% | 0.07% | 0.08% |
| Impurity C | Not specified | ND | ND | ND | ND |
| Impurity D | Not specified | ND | ND | ND | ND |
| Any single unspecified Impurity | NMT 0.5% | 0.06% | 0.06% | 0.07% | 0.06% |
| Total Impurity | NMT 2% | 0.17% | 0.19% | 0.20% | 0.19% |
| Assay of Timolol | 90%-110% | 102.10% | 101.90% | 102.80% | 102.70% |
| Impurity of Timolol | | | | | |
| Timolol Impurity - 1 | NMT 0.15% | ND | ND | ND | ND |
| Any single unspecified Impurity | NMT 0.5% | 0.03% | 0.02% | 0.02% | 0.03% |
| Total Impurity | Not more than 1.5% | 0.03% | 0.02% | 0.02% | 0.03% |
| pH | TBE | 6.08 | 6.07 | 6.07 | 6.07 |
| Osmolality | 260 to 330 mOsm/kg | 315 | 314 | 315 | 311 |

ND: Not Detected;
NMT: Not More Than;
RH: Relative Humidity;
TBE: To Be Established Results:
The Results of Stress Stability at 50° C. for 4 Weeks for Formulation 3:

The brinzolamide content is measured to be 100.1% (Limit: 90.0-110.0%) which is in the acceptable limit range, all the known impurities (Impurity A; B; C & D) are well within the acceptable limit range as shown in table 1 and total impurity is measured to be 0.2% (Limit: NMT 2.0%) which is in the acceptable limit range.

The timolol content is measured to be 102.8% (Limit: 90.0-110.0%) which is in the acceptable limit range, the known impurity (Impurity 1) is below detection level and total impurity is measured to be 0.02% (Limit: NMT 1.5%) which is in the acceptable limit range.

The Results of Accelerated Stability at 40° C. and NMT 25% RH for One Month for Formulation 3:

The brinzolamide content is measured to be 100% (Limit: 90.0-110.0%) which is in the acceptable limit range, all the known impurities (Impurity A; B; C & D) are well within the acceptable limit range as shown in table 1 and total impurity is measured to be 0.19% (Limit: NMT 2.0%) which is in the acceptable limit range.

The timolol content is measured to be 102.7% (Limit: 90.0-110.0%) which is in the acceptable limit range, the known impurity (Impurity 1) is below detection level and total impurity is measured to be 0.03% (Limit: NMT 1.5%) which is in the acceptable limit range.

Rest all other parameters such as pH; Osmolality and the physical parameters are well within the specifications i.e. as per the label claim.

Hence it is concluded from the above stability data that all the formulations are stable and well within the specifications.

UTILITY OF THE INVENTION

The present inventors provides an aqueous sterile, ophthalmic pharmaceutical formulation comprising a carbonic anhydrase inhibitor or its pharmaceutically acceptable salt as an active agent and a polymer and a second or, third therapeutically active agent optionally along with pharmaceutically acceptable excipients and/or mixtures thereof. The present formulation is to be utilized for lowering intraocular pressure in a patient suffering from elevated intraocular pressure or, glaucoma.

We claim:

1. An aqueous sterile, ophthalmic pharmaceutical formulation, comprising:
   (A) brinzolamide, or a pharmaceutically acceptable salt thereof, as an active agent in an amount of from 0.3-0.5 w/w % of the formulation,
   (B) polyvinyl caprolactam-polyvinyl acetate-polyethylene glycol graft copolymer, in an amount of from 0.4-0.8 w/w % of the formulation,
   (C) polysorbate 80, in an amount of 1.0 w/w % of the formulation;
   (D) an additional therapeutically active agent, which is latanoprost, wherein the latanoprost is present in an amount of 0.005 w/w % of the formulation;

(E) edetate disodium, in an amount of 0.01 w/w % of the formulation;
(F) mannitol, in an amount of 3.3 w/w % of the formulation;
(G) carbomer, in an amount of 0.4-0.45 w/w % of the formulation; and
(H) sodium chloride, in an amount of 0.19 w/w % of the formulation;
wherein the formulation is a solution and the formulation pH is from 5.5 to 8.

2. The formulation of claim 1, wherein the solution is in the form of drops.

3. An aqueous sterile, ophthalmic pharmaceutical formulation, comprising:
(A) brinzolamide, or a pharmaceutically acceptable salt thereof, as an active agent in an amount of 0.5 w/w % of the formulation,
(B) polyvinyl caprolactam-polyvinyl acetate-polyethylene glycol graft copolymer, in an amount of 0.8 w/w % of the formulation,
(C) polysorbate 80, in an amount of 1.0 w/w % of the formulation;
(D) an additional therapeutically active agent, which is timolol, wherein the timolol is present in an amount of 0.5 w/w % of the formulation;
(E) edetate disodium, in an amount of 0.01 w/w % of the formulation;
(F) mannitol, in an amount of 3 w/w % of the formulation;
(G) carbomer, in an amount of 0.42 w/w % of the formulation; and
(H) sodium chloride, in an amount of 0.1 w/w % of the formulation;
wherein the formulation is a solution and the formulation pH is from 5.5 to 8.

4. An aqueous sterile, ophthalmic pharmaceutical formulation, comprising:
(A) brinzolamide, or a pharmaceutically acceptable salt thereof, as an active agent in an amount of 0.5 w/w % of the formulation,
(B) polyvinyl caprolactam-polyvinyl acetate-polyethylene glycol graft copolymer, in an amount of 0.8 w/w % of the formulation,
(C) polysorbate 80, in an amount of 1.0 w/w % of the formulation;
(D) an additional therapeutically active agent, which is timolol, wherein the timolol is present in an amount of 0.5 w/w % of the formulation;
(E) edetate disodium, in an amount of 0.01 w/w % of the formulation;
(F) mannitol, in an amount of 2.5 w/w % of the formulation;
(G) carbomer, in an amount of 0.42 w/w % of the formulation;
(H) boric acid, in an amount of 0.19 w/w % of the formulation;
(I) sodium borate, in an amount of 0.01 w/w % of the formulation;
(J) zinc chloride, in an amount of 0.10 w/w % of the formulation;
(K) sodium metabisulphate, in an amount of 0.2 w/w % of the formulation; and
wherein the formulation is a solution and the formulation pH is from 5.5 to 8.

5. The formulation of claim 3, wherein the solution is in the form of drops.

6. The formulation of claim 4, wherein the solution is in the form of drops.

7. A method of treating elevated intraocular pressure in a patient with glaucoma or ocular hypertension, the method comprising administering to the patient the ophthalmic formulation of claim 1.

8. The method of claim 7, wherein the formulation is administered once a day, twice a day, or three times a day to each eye in need thereof.

9. A method of treating elevated intraocular pressure in a patient with glaucoma or ocular hypertension, the method comprising administering to the patient the ophthalmic formulation of claim 3.

10. The method of claim 9, wherein the formulation is administered once a day, twice a day, or three times a day to each eye in need thereof.

11. A method of treating elevated intraocular pressure in a patient with glaucoma or ocular hypertension, the method comprising administering to the patient the ophthalmic formulation of claim 4.

12. The method of claim 11, wherein the formulation is administered once a day, twice a day, or three times a day to each eye in need thereof.

* * * * *